United States Patent
Rottländer et al.

(10) Patent No.: US 7,393,845 B2
(45) Date of Patent: Jul. 1, 2008

(54) HETEROARYL DERIVATES, THEIR PREPARATION AND USE

(75) Inventors: Mario Rottländer, Greve (DK); Ejner Knud Moltzen, Gentofte (DK); Ivan Mikkelsen, Koge (DK); Thomas Ruhland, Roskilde (DK); Kim Andersen, Virum (DK); Christian Krog-Jensen, Rungsted Kyst (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 11/758,511

(22) Filed: Jun. 5, 2007

(65) Prior Publication Data

US 2008/0027071 A1 Jan. 31, 2008

Related U.S. Application Data

(63) Continuation of application No. 10/482,764, filed as application No. PCT/DK02/00435 on Jun. 27, 2002, now abandoned.

(30) Foreign Application Priority Data

Jun. 29, 2001 (DK) ............................. 2001 01036

(51) Int. Cl.
  *A61K 31/536* (2006.01)
  *A61K 31/496* (2006.01)
  *C07D 405/12* (2006.01)
  *C07D 413/12* (2006.01)

(52) U.S. Cl. .............. 514/230.5; 514/252.2; 514/253.1; 544/105; 544/295; 544/364; 544/318; 544/333; 546/194; 546/256; 540/575; 540/597; 540/598; 540/599; 540/600

(58) Field of Classification Search .............. None
See application file for complete search history.

(56) References Cited

U.S. PATENT DOCUMENTS 5,225,409 A   7/1993  Taverne et al.
2006/0258678 A1  11/2006  Rottlander et al.

OTHER PUBLICATIONS

Jones et al, Pharmacology, Biochem and Behav 2002, vol. 71, p. 555-568.
Robichaud et al, Annual Reports in Medicinal Chemistry 2000, vol. 36, p. 11-20.
TenBrink et al., J Med Chem 1996, vol. 39, p. 2435-2437.
Van Steen, B. J. "Structure activity relationship studies on 5-HT1A receptor ligands. 2. Heterocyclic Phenylpiperazines with N4-aralkylsubstituents" J. Med Chem 1994, vol. 37, p. 2761-2773.

*Primary Examiner*—Emily Bernhardt
(74) *Attorney, Agent, or Firm*—Stephen G. Kalinchak; Margaret M. Buck; Kitae Lim

(57) ABSTRACT

A heteroaryl derivative having the formula (I). The compounds of the invention are considered useful for the treatment of affective disorders such as general anxiety disorder, panic disorder, obsessive compulsive disorder, depression, social phobia and eating disorders, and neurological disorders such as psychosis

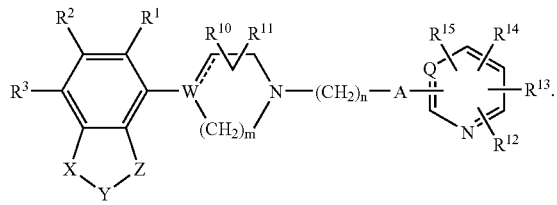

(I)

17 Claims, No Drawings

HETEROARYL DERIVATES, THEIR PREPARATION AND USE

This application is a continuation application of U.S. Ser. No. 10/482,764 filed Jul. 6, 2004, now abandoned, which is a 371 application of PCT/DK02/00435, filed Jun. 27, 2002, and claims benefit of priority under 35 U.S.C. § 119(a)-(d) of Danish application number PA 2001 01036, filed Jun. 29, 2001, the contents of all of which are hereby incorporated by reference.

The present invention relates to novel heteroaryl derivatives potently binding to the 5-$HT_{1A}$ receptor, pharmaceutical compositions containing these compounds and the use thereof for the treatment of certain psychiatric and neurological disorders. Many of the compounds of the invention have also potent serotonin reuptake inhibition activity and are thus considered particularly useful for the treatment of depression.

Furthermore, many compounds of the invention have also effect at dopamine $D_3$ and $D_4$ receptors and are considered to be useful for the treatment of psychosis.

BACKGROUND ART

Clinical and pharmacological studies have shown that 5-$HT_{1A}$ agonists and partial agonists are useful in the treatment of a range of affective disorders such as generalised anxiety disorder, panic disorder, obsessive compulsive disorder, depression and aggression.

It has also been reported that 5-$HT_{1A}$ ligands may be useful in the treatment of ischaemia.

An overview of 5-$HT_{1A}$ antagonists and proposed potential therapeutic targets for these antagonists based upon preclinical and clinical data are presented by Schechter et al., *Serotonin* 1997, Vol. 2, Issue 7. It is stated that 5-$HT_{1A}$ antagonists may be useful in the treatment of schizophrenia, senile dementia, dementia associated with Alzheimer's disease, and in combination with SSRI antidepressants also to be useful in the treatment of depression.

5-HT reuptake inhibitors are well-known antidepressant drugs and useful for the treatment of panic disorders and social phobia.

The effect of combined administration of a compound that inhibits serotonin reuptake and a 5-$HT_{1A}$ receptor antagonist has been evaluated in several studies (Innis, R. B. et al. *Eur. J. Pharmacol.* 1987, 143, p 195-204 and Gartside, S. E., *Br. J. Pharmacol.* 1995, 115, p 1064-1070, Blier, P. et al. *Trends Pharmacol. Sci.* 1994, 15, 220). In these studies it was found that combined 5-$HT_{1A}$ receptor antagonists and serotonin reuptake inhibitors would produce a more rapid onset of therapeutic action.

Dopamine $D_4$ receptors belong to the family of dopamine $D_2$-like receptors which is considered to be responsible for the antipsychotic effects of neuroleptics. Dopamine $D_4$ receptors are primarily located in areas of the brain other than striatum, suggesting that dopamine $D_4$ receptor ligands have antipsychotic effect and are devoid of extrapyramidal activity.

Accordingly, dopamine $D_4$ receptor ligands are potential drugs for the treatment of psychosis and positive symptoms of schizophrenia and compounds with combined effects at dopamine $D_4$, and serotonergic receptors may have the further benefit of improved effect on negative symptoms of schizophrenia, such as anxiety and depression, alcohol abuse, impulse control disorders, aggression, side effects induced by conventional antipsychotic agents, ischaemic disease states, migraine, senile dementia and cardiovascular disorders and in the improvement of sleep.

Dopamine $D_3$ receptors also belong to the family of dopamine $D_2$ like receptors. $D_3$ antagonistic properties of an antipsychotic drug could reduce the negative symptoms and cognitive deficits and result in an improved side effect profile with respect to BPS and hormonal changes.

Accordingly, agents acting on the 5-$HT_{1A}$ receptor, both agonists and antagonists, are believed to be of potential use in the therapy of psychiatric and neurological disorders and thus being highly desired. Furthermore, antagonists at the same time having potent serotonin reuptake inhibition activity and/or $D_4$ and/or $D_3$ activity may be particularly useful for the treatment of various psychiatric and neurological diseases.

Bart J van Steen et al. *J. Med. Chem.* 1994, 37(17), 2761-73 describes certain related benzofuran and benzodioxan derivatives having affinity for the 5-$HT_{1A}$ receptor and therefore being useful in the treatment of depression and anxiety.

SUMMARY OF THE INVENTION

It has now been found that compounds of a certain class of heteroaryl derivatives bind to the 5-$HT_{1A}$ receptor with high affinities. Additionally, the compounds also show serotonin reuptake inhibition activity. Furthermore, it has been found that many of the compounds have effect at dopamine $D_3$ and/or $D_4$ receptors.

Accordingly, the present invention relates to novel compounds of the general Formula I:

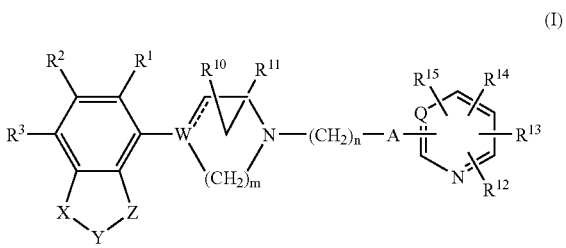

wherein
X represents O, $NR^{16}$, S or $CR^4R^5$.
Y is —$CR^6R^7$—, —$CR^6R^7$—$CR^8R^9$—, —$CR^6$═$CR^7$— or CO—$CR^6R^7$; or
X and Y together form a group —$CR^4$═$CR^5$— or —$CR^4$═$CR^5$—$CR^6R^7$—;
Z represents O or S;
n is 2, 3, 4, 5, 6, 7, 8, 9 or 10;
m is 2 or 3:
A is O or S;
W is N, C or CH;
Q is N, C or CH;
wherein the dotted line means an optional bond;
$R^1$-$R^9$ are each independently selected from hydrogen, halogen, nitro, cyano, trifluoromethyl, trifluoromethoxy, $C_{1-6}$-alkyl $C_{2-6}$-alkenyl $C_{2-6}$-alkynyl, $C_{3-8}$-cycloalkyl, $C_{3-8}$-cycloalkyl-$C_{1-6}$-alkyl, aryl-$C_{1-6}$-alkyl $C_{1-6}$-alkoxy, $C_{1-6}$-alkylthio, hydroxy, formyl, acyl, amino, $C_{1-6}$-alkylamino, di($C_{1-6}$-alkyl)amino, acylamino, $C_{1-6}$-alkoxycarbonylamino, aminocarbonylamino, $C_{1-6}$-alkylaminocarbonylamino and di($C_{1-6}$-alkyl)amiocarbonylamino; and
$R^{16}$ is selected from hydrogen, halogen, nitro, cyano, trifluoromethyl, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, formyl, acyl; and $R^{10}$ and $R^{11}$ are each independently selected from hydrogen and $C_{1-6}$-alkyl or may together form a bridge consisting of two or three methylene groups; and $R^{12}$, $R^{13}$, $R^{14}$ and $R^{15}$ are each independently selected from hydrogen, halogen, nitro, cyano, trifluoromethyl, trifluoromethoxy, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, heteroaryl, $C_{1-6}$-alkoxy, $C_{1-6}$-alkylthio, $C_{1-6}$-alkylsulphonyl, hydroxy, formyl, acyl, amino, acylamino, aminocarbonyl, $C_{1-6}$-alkoxycarbonylamino, aminocarbonylamino, $C_{1-6}$-alkylaminocarbonylamino, di($C_{1-6}$-alkyl)aminocarbonylamino, $SO_2NR^{20}R^{21}$ and $NR^{20}R^{21}$ wherein $R^{20}$ and $R^{21}$ independently represent hydrogen, $C_{1-6}$-alkyl, $C_{3-8}$-cycloalkyl or phenyl; or $R^{20}$ and $R^{21}$ together with the nitrogen to which they are attached form a 5- or 6-membered ring optionally containing one further heteroatom, which ring may optionally be substituted by $C_{1-6}$-alkyl or acyl;

any of its enantiomers or any mixture thereof, or an acid addition salt thereof.

The invention also relates to a pharmaceutical composition comprising a compound of formula (I) or a pharmaceutically acceptable salt thereof and at least one pharmaceutically acceptable carrier or diluent.

In a further embodiment, the invention relates to the use of a compound of formula (I) or a pharmaceutically acceptable acid addition salt thereof for the preparation of a medicament for the treatment of a disorder or disease responsive to the inhibition of serotonin uptake and antagonism of 5-$HT_{1A}$ receptors.

In a further embodiment, the invention relates to the use of a compound of formula (I) or a pharmaceutically acceptable acid addition salt thereof for the preparation of a medicament for the treatment of a disorder or disease responsive to the combined effect of 5-$HT_{1A}$ receptors and dopamine $D_4$ receptors.

In particular, the invention relates to the use of a compound according to the invention or a pharmaceutically acceptable acid addition salt thereof for the preparation of a medicament for the treatment of affective disorders such as general anxiety disorder, panic disorder, obsessive compulsive disorder, depression, social phobia and eating disorders; other psychiatric disorders such as psychosis and neurological disorders.

In still another embodiment, the present invention relates to a method for the treatment of a disorder or disease of living animal body, including a human, which is responsive to the inhibition of serotonin uptake and antagonism of 5-$HT_{1A}$ receptors comprising administering to such a living animal body, including a human, a therapeutically effective amount of a compound of formula (I) or a pharmaceutically acceptable acid addition salt thereof.

In still another embodiment, the present invention relates to a method for the treatment of a disorder or disease of living animal body, including a human, which is responsive to the effect of 5-$HT_{1A}$ and $D_4$ receptors comprising administering to such a living animal body, including a human, a therapeutically effective amount of a compound of formula (I) or a pharmaceutically acceptable acid addition salt thereof.

Due to their combined antagonism of 5-$HT_{1A}$ receptors and serotonin reuptake inhibiting effect, the compounds of the invention are considered particularly useful as fast onset of action medicaments for the treatment of depression. The compounds may also be useful for the treatment of depression in patients who are resistant to treatment with currently available antidepressants.

The compounds of the invention have high affinity for the 5-$HT_{1A}$ and $D_4$ receptors. Accordingly, the compounds of the invention are considered useful for the treatment of affective disorders such as general anxiety disorder, panic disorder, obsessive compulsive disorder, depression, social phobia and eating disorders; other psychiatric disorders such as psychosis and neurological disorders.

DETAILED DESCRIPTION OF THE INVENTION

In preferred embodiments of the invention, Z is O.

In preferred embodiments of the invention, Y is —$CH_2CH_2$— or —$CH_2CO$—.

In preferred embodiments of the invention, X is O or NH.

In preferred embodiments of the invention, W is N.

In preferred embodiments of the invention, m is 2.

In a further embodiment of the invention, n is 2, 3 or 4.

In a more preferred embodiment of the invention, n is 2.

In preferred embodiments of the invention, $R^1$, $R^2$ and $R^3$ independently represent hydrogen, halogen or CN.

In a further embodiment of the invention, $R^{12}$, $R^{13}$, $R^{14}$, $R^{15}$ and $R^{16}$ are independently selected from a group consisting of hydrogen, heteroaryl, trifluoromethyl, cyano, $C_{1-6}$-alkyl, halogen, $NR^{20}R^{21}$, $SO_2NR^{20}R^{21}$, aryl, $C_{1-6}$-alkylsulfonyl and carbonylamino.

In a preferred embodiment of the invention, $R^{12}$, $R^{13}$, $R^{14}$, $R^{15}$ and $R^{16}$ are independently selected from hydrogen, thiophen, trifluoromethyl, cyano, methyl, ethyl, cyclopropyl, chloro, bromo, fluoro, piperazine, 1-piperazine-4-methyl, 1-piperidine, 1-piperidinyl-sulfonyl, methanesulfonyl, methylsulfid, phenyl and carbonylamino.

Specific compounds of the invention are compounds selected from:

2-{2-[4-(2,3-Dihydrobenzo[1,4]dioxin-5-yl)piperazin-1-yl]ethylsulfanyl}-6-methylnicotinonitrile, 1a 2-{2-[4-(2,3-Dihydrobenzo[1,4]dioxin-5-yl)piperazin-1-yl]ethylsulfanyl}-6-methyl-4-trifluoromethylnicotinonitrile, 1b 2-{2-[4-(8-Cyano-2,3-dihydrobenzo[1,4]dioxin-5-yl)piperazin-1-yl]ethylsulfanyl}-6-methyl-4-trifluoromethylnicotinonitrile, 1c 2-{2-[4-(2,3-Dihydrobenzo[1,4]dioxin-5-yl)piperazin-1-yl]ethylsulfanyl}-6-(thiophen-2-yl)-4-trifluoromethylnicotinonitrile, 1d {2-[4-(8-Cyano-2,3-dihydrobenzo[1,4]dioxin-5-yl)piperazin-1-yl]ethylsulfanyl}-6-methylnicotinonitrile, 1e 3-{2-[4-(2,3-Dihydrobenzo[1,4]dioxin-5-yl)piperazin-1-yl]ethoxy}-2-methylpyridine, 1f 2-Chloro-3-{2-[4-(2,3-dihydrobenzo[1,4]dioxin-5-yl)piperazin-1-yl]-ethoxy}pyridine, 1g 2-Bromo-3-{2-[4-(2,3-dihydrobenzo[1,4]dioxin-5-yl)piperazin-1-yl]ethoxy}pyridine, 1h 3-Chloro-5-{2-[4-(2,3-dihydrobenzo[1,4]dioxin-5-yl)piperazin-1-yl]ethoxy}pyridine, 1i 2-Chloro-3-{2-[4-(8-cyano-2,3-dihydrobenzo[1,4]dioxin-5-yl)piperazin-1-yl]ethoxy}pyridine, 1j 2-Bromo-3-{2-[4-(8-Cyano-2,3-dihydrobenzo[1,4]dioxin-5-yl)piperazin-1-yl]ethoxy}pyridine, 1k 3-Chloro-5-{2-[4-(8-cyano-2,3-dihydrobenzo[1,4]dioxin-5-yl)piperazin-1-yl]ethoxy}pyridine, 1l 3-{2-[4-(8-Cyano-2,3-dihydrobenzo[1,4]dioxin-5-yl)piperazin-1-yl]ethoxy}-2-methylpyridine, 1m 4-{2-[4-(8-Cyano-2,3-dihydrobenzo[1,4]dioxin-5-yl)piperazin-1-yl]ethylsulfanyl}-3-(piperidin-1-ylsulfonyl)pyridine, 1n 4-{2-[4-(2,3-Dihydrobenzo[1,4]dioxin-5-yl)piperazin-1-yl]ethylsulfanyl}-3-(piperidin-1-ylsulfonyl)pyridine, 1o 2-{4-[4-(2,3-Dihydrobenzo[1,4]dioxin-5-yl)piperazin-1-yl]butylsulfanyl}-5-trifluoromethylpyridine, 1p 2-{4-[4-(8-Cyano-2,3-dihydrobenzo[1,4]dioxin-5-yl)piperazin-1-yl]butylsulfanyl}-5-trifluoromethylpyridine, 1q 2-{4-[4-(8-Cyano-2,3-dihydrobenzo[1,4]dioxin-5-yl)piperazin-1-yl]butylsulfanyl}-5-trifluoromethylpyridine, 1r 2-{3-[4-(2,3-Dihydrobenzo[1,4]dioxin-5-yl)piperazin-1-yl]propylsulfanyl}-5-trifluoromethylpyridine, 1s 2-{3-[4-(2,3-Dihydrobenzo[1,4]dioxin-5-yl)piperazin-1-yl]propylsulfanyl}-4,6-dimethylnicotinonitrile, 1t 2-{3-[4-(2,3-Dihydrobenzo[1,4]dioxin-5-yl)piperazin-1-yl]butylsulfanyl}-4,6-dimethylnicotinonitrile, 1u 2-{3-[4-(8-Cyano-2,3-dihydrobenzo[1,4]dioxin-5-yl)piperazin-1-yl]propylsulfanyl}-5-trifluoromethylpyridine, 1v 2-{3-[4-(8-Cyano-2,3-dihydrobenzo[1,4]dioxin-5-yl)piperazin-1-yl]propylsulfanyl}-4,6-dimethylnicotinonitrile, 1x 2-{2-[4-(2,3-Dihydrobenzo[1,4]dioxin-5-yl)piperazin-1-yl]ethylsulfanyl}nicotinonitrile, 2a 2-{2-[4-(8-Cyano-2,3-dihydrobenzo[1,4]dioxin-5-yl)piperazin-1-yl]ethylsulfanyl}-3-methanesulfonylmethyl-6-phenylpyridine, 2b 2-{2-[4-(8-Cyano-2,3-dihydrobenzo[1,4]dioxin-5-yl)piperazin-1-yl]ethylsulfanyl}-4-methyl-6-piperidin-1-yl)nicotinonitrile, 2c 2-{2-[4-(8-Cyano-2,3-dihydrobenzo[1,4]dioxin-5-yl)piperazin-1-yl]ethylsulfanyl}-6-methylnicotinamide, 2d 2-{2-[4-(8-Cyano-2,3-dihydrobenzo[1,4]dioxin-5-yl)piperazin-1-yl]ethylsulfanyl}nicotinonitrile, 2e 4-Cyano-2-{2-[4-(2,3-dihydrobenzo[1,4]dioxin-5-yl)piperazin-1-yl]ethoxy}pyridine, 2f 2-{2-[4-(2,3-Dihydrobenzo[1,4]dioxin-5-yl)piperazin-1-yl]ethoxy}-6-methylnicotinamide, 2g 2-{2-[4-(2,3-Dihydrobenzo[1,4]dioxin-5-yl)piperazin-1-yl]ethoxy)-4-methyl-6-piperidin-1-yl)nicotinonitrile, 2h 2-{2-[4-(2,3-Dihydrobenzo[1,4]dioxin-5-yl)piperazin-1-yl]ethoxy)-4-methyl-6-(4-methylpiperazin-1-yl)nicotinonitrile, 2i 6-Cyclopropyl-2-{2-[4-(2,3-dihydrobenzo[1,4]dioxin-5-yl)piperazin-1-yl]ethoxy)-4-trifluoromethylnicotinonitrile, 2j 2-{2-[4-(2,3-Dihydrobenzo[1,4]dioxin-5-yl)piperazin-1-yl]ethoxy}-3-methanesulfonyl-4-methyl-6-phenylpyridine, 2k 2-{3-[4-(2,3-Dihydrobenzo[1,4]dioxin-5-yl)piperazin-1-yl]ethylsulfanyl}-4,6-dimethyl-3-phenylsulfonylpyridine, 2l 2-{2-[4-(8-Cyano-2,3-dihydrobenzo[1,4]dioxin-5-yl)piperazin-1-yl]ethylsulfanyl}pyridine, 2m 2-{3-[4-(2,3-Dihydrobenzo[1,4]dioxin-5-yl)piperazin-1-yl]ethylsulfanyl}-4,6-dimethylnicotinonitrile, 2n 6-Chloro-2-{3-[4-(2,3-dihydrobenzo[1,4]dioxin-5-yl)piperazin-1-yl]ethylsulfanyl}-4-methylnicotinonitrile, 2o 5-Chloro-2-{3-[4-(2,3-dihydrobenzo[1,4]dioxin-5-yl)piperazin-1-yl]ethylsulfanyl}nicotinonitrile, 2p 6-Chloro-2-{3-[4-(2,3-dihydrobenzo[1,4]dioxin-5-yl)piperazin-1-yl]ethylsulfanyl}nicotinonitrile, 2q 6-Chloro-2-{3-[4-(2,3-dihydrobenzo[1,4]dioxin-5-yl)piperazin-1-yl]ethylsulfanyl}-5-fluoronicotinonitrile, 2r 2-{3-[4-(8-Cyano-2,3-dihydrobenzo[1,4]dioxin-5-yl)piperazin-1-yl]ethylsulfanyl}-4,6-dimethylnicotinonitrile, 2s 6-Chloro-2-{3-[4-(8-cyano-2,3-dihydrobenzo[1,4]dioxin-5-yl)piperazin-1-yl]ethylsulfanyl}-4-methylnicotinonitrile, 2t 5-Chloro-2-{3-[4-(8-cyano-2,3-dihydrobenzo[1,4]dioxin-5-yl)piperazin-1-yl]ethylsulfanyl}-4,6-dimethylnicotinonitrile, 2u 5-Chloro-2-{3-[4-(8-cyano-2,3-dihydrobenzo[1,4]dioxin-5-yl)piperazin-1-yl]ethylsulfanyl}nicotinonitrile, 2v 6-Chloro-2-{3-[4-(8-cyano-2,3-dihydrobenzo[1,4]dioxin-5-yl)piperazin-1-yl]ethylsulfanyl}nicotinonitrile, 2x 6-Chloro-2-{3-[4-(8-cyano-2,3-dihydrobenzo[1,4]dioxin-5-yl)piperazin-1-yl]ethylsulfanyl}-5-fluoronicotinonitrile, 2y 2-[2-[4-(6-Chloro-2,3-dihydro-1,4-benzoxazin-3-on-8-yl)piperazin-1-yl]ethylsulfanyl]nicotinonitrile, 2z 2-[2-[4-(6-Chloro-2,3-dihydro-1,4-benzoxazin-3-on-8-yl)piperazin-1-yl]ethylsulfanyl]-4,6-dimethylnicotinonitrile, 2aa 6-Chloro-2-[2-[4-(6-chloro-2,3-dihydro-1,4-benzoxazin-3-on-8-yl)piperazin-1-yl]ethylsulfanyl]-4-methylnicotinonitrile, 2ab 4-Chloro-2-[2-[4-(6-chloro-2,3-dihydro-1,4-benzoxazin-3-on-8-yl)piperazin-1-yl]ethylsulfanyl]-6-methylnicotinonitrile, 2ac 5-Chloro-2-[2-[4-(6-chloro-2,3-dihydro-1,4-benzoxazin-3-on-8-yl)piperazin-1-yl]ethylsulfanyl]-4,6-dimethylnicotinonitrile, 2ad 5-Chloro-2-[2-[4-(6-chloro-2,3-dihydro-1,4-benzoxazin-3-on-8-yl)piperazin-1-yl]ethylsulfanyl]nicotinonitrile, 2ae 6-Chloro-2-[2-[4-(6-chloro-2,3-dihydro-1,4-benzoxazin-3-on-8-yl)piperazin-1-yl]ethylsulfanyl]nicotinonitrile, 2af 6-Chloro-2-[2-[4-(6-chloro-2,3-dihydro-1,4-benzoxazin-3-on-8-yl)piperazin-1-yl]ethylsulfanyl]-5-fluoronicotinonitrile, 2ag 2-[2-[4-(6-Chloro-2,3-dihydro-1,4-benzoxazin-8-yl)piperazin-1-yl]ethylsulfanyl]nicotinonitrile, 2ah 2-[2-[4-(6-Chloro-2,3-dihydro-1,4-benzoxazin-8-yl)]ethylsulfanyl]-4,6-dimethylnicotinonitrile, 2ai 6-Chloro-2-[2-[4-(6-chloro-2,3-dihydro-1,4-benzoxazin-8-yl)piperazin-1-yl]ethylsulfanyl]-4-methylnicotinonitrile, 2aj 4-Chloro-2-[2-[4-(6-chloro-2,3-dihydro-1,4-benzoxazin-8-yl)piperazin-1-yl]ethylsulfanyl]-6-methylnicotinonitrile, 2ak 5-Chloro-2-[2-[4-(6-chloro-2,3-dihydro-1,4-benzoxazin-8-yl)piperazin-1-yl]ethylsulfanyl]-4,6-dimethylnicotinonitrile, 2al 5-Chloro-2-[2-[4-(6-chloro-2,3-dihydro-1,4-benzoxazin-8-yl)piperazin-1-yl]ethylsulfanyl]nicotinonitrile, 2am 6-Chloro-2-[2-[4-(6-chloro-2,3-dihydro-1,4-benzoxazin-8-yl)piperazin-1-yl]ethylsulfanyl]nicotinonitrile, 2an 6-Chloro-2-[2-[4-(6-chloro-2,3-dihydro-1,4-benzoxazin-8-yl)piperazin-1-yl]ethylsulfanyl]-5-fluoronicotinonitrile, 2ao 5-Cyano-4-{2-[4-(2,3-dihydrobenzo[1,4]dioxin-5-yl)piperazin-1-yl]ethylsulfanyl}pyrimidine, 2ap 5-Cyano-4-{2-[4-(2,3-dihydrobenzo[1,4]dioxin-5-yl)piperazin-1-yl]ethylsulfanyl}-6-methylsulfanyl-2-phenylpyrimidine, 2aq 5-Cyano-4-{2-[4-(8-cyano-2,3-dihydrobenzo[1,4]dioxin-5-yl)piperazin-1-yl]ethylsulfanyl}pyrimidine, 2ar 5-Cyano-4-{2-[4-(8-cyano-2,3-dihydrobenzo[1,4]dioxin-5-yl)piperazin-1-yl]ethylsulfanyl}-6-methylsulfanyl-2-phenylpyrimidine, 2as 2-{2-[4-(2,3-Dihydrobenzo[1,4]dioxin-5-yl)piperazin-1-yl]ethylsulfanyl}-4,6-dimethylpyrimidine, 2at 2-{2-[4-(8-Cyano-2,3-dihydrobenzo[1,4]dioxin-5-yl)piperazin-1-yl]ethylsulfanyl}-4,6-dimethylpyrimidine, 2au 2-{2-[4-(2,3-Dihydrobenzo[1,4]dioxin-5-yl)piperazin-1-yl]ethylsulfanyl}-4-methoxynicotinonitrile, 2av 6-Chloro-2-{2-[4-(2,3-dihydrobenzo[1,4]dioxin-5-yl)piperazin-1-yl]ethylsulfanyl}-5-fluoronicotinonitrile, 2ax 6-Chloro-2-{2-[4-(8-cyano-2,3-dihydrobenzo[1,4]dioxin-5-yl)piperazin-1-yl]ethylsulfanyl}-5-fluoronicotinonitrile, 2ay 2-{2-[4-(2,3-Dihydrobenzo[1,4]dioxin-5-yl)piperazin-1-yl]ethylsulfanyl}-5-ethylpyrimidine, 2az 2-{2-[4-(2,3-Dihydrobenzo[1,4]dioxin-5-yl)piperazin-1-yl]ethylsulfanyl}-4-trifluoromethylpyrimidine, 2ba 2-{2-[4-(2,3-Dihydrobenzo[1,4]dioxin-5-yl)piperazin-1-yl]ethylsulfanyl}-4,6-dimethoxypyrimidine, 2bb 4-Chloro-2-{2-[4-(8-cyano-2,3-dihydrobenzo[1,4]dioxin-5-yl)piperazin-1-yl]ethylsulfanyl}-6-methylpyrimidine, 2bc 2-{2-[4-(8-Cyano-2,3-dihydrobenzo[1,4]dioxin-5-yl)piperazin-1-yl]ethylsulfanyl}-4-trifluoromethylpyrimidine, 2bd Some of the compounds of general Formula I may exist as optical isomers thereof and such optical isomers are also embraced by the invention.

The term $C_{1-6}$ alkyl refers to a branched or unbranched alkyl group having from one to six carbon atoms inclusive, such as methyl, ethyl 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms inclusive.

Halogen means fluoro, chloro, bromo or iodo.

The term $C_{3-8}$ cycloalkyl designates a monocyclic or bicyclic carbocycle having three to eight C-atoms, such as cyclopropyl, cyclopentyl, cyclohexyl, cycloheptyl, and cyclooctyl.

The terms $C_{1-6}$ alkoxy, $C_{1-6}$ alkylthio and $C_{1-6}$ alkylsulphonyl designate such groups in which the alkyl group is $C_{1-6}$ alkyl as defined above.

The term aryl designates an aromatic hydrocarbon such as phenyl or naphtyl.

The term heteroaryl refers to a mono- or bicyclic heterocyclic aromatic group containing at least one N, S or O atom, such as furyl, pyrrolyl, thienyl, oxazolyl, isoxazolyl, thiazolyl, isothiazolyl, imidazolyl, pyridyl, pyrimidyl, tetrazolyl, benzofuranyl, benzothienyl, benzimidazolyl, indolyl. Preferred heteroaryls are monocyclic aryls. Especially preferred are thienyl and piperidinyl.

Acyl means —CO-alkyl wherein the alkyl group is $C_{1-6}$ alkyl as defined above.

Amino means $NH_2$.

$C_{1-6}$ alkylamino means —NH-alkyl and di($C_{1-6}$-alkyl)amino means —N-(alkyl)$_2$ where the alkyl group is $C_{1-6}$ alkyl as defined above.

Acylamino means —NH-acyl wherein acyl is as defined above.

Carbonylamino means —CONH—

$C_{1-6}$ alkoxycarbonylamino means alkyl-O—CO—NH— wherein the alkyl group is $C_{1-6}$ alkyl as defined above.

$C_{1-6}$ alkylaminocarbonylamino means alkyl-NH—CO—NH— wherein the alkyl group is $C_{1-6}$ alkyl as defined above.

di($C_{1-6}$-alkyl)aminocarbonylamino means (alkyl)$_2$-N—CO—NH— wherein the alkyl group is $C_{1-6}$ alkyl as defined above.

As used herein, a phenyl group which may be substituted means a phenyl group which may be substituted one or more times with a substituent selected form halogen, trifluoromethyl, cyano, nitro, amino, $C_{1-6}$-alkylamino, di($C_{1-6}$-alkyl)amino, $C_{1-6}$-alkyl, $C_{1-6}$-alkoxy and hydroxy.

Exemplary of organic acid addition salts according to the invention are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of inorganic acid addition salts according to the invention are those with hydrochloric, hydrobromic, sulfuric, sulfamic, phosphoric, and nitric acids. The acid addition salts of the invention are preferably pharmaceutically acceptable salts formed with non-toxic acids.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (e.g. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallisation of d- or l-(tartrates, mandelates or camphorsulphonate) salts for example. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981).

Optically active compounds can also be prepared from optically active starting materials.

The compounds of the invention can be prepared by one of the following methods comprising:

a) treating a compound of formula (II) with a compound of formula (III) in the presence of a reducing agent.

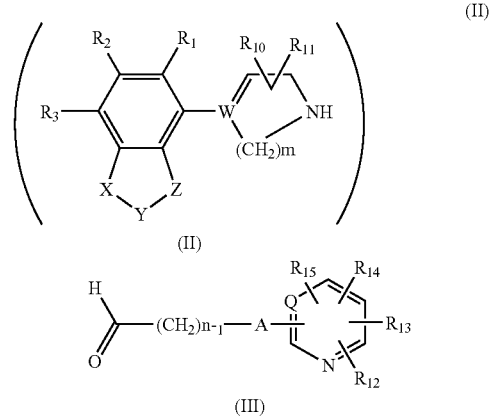

wherein n, m, $R^1$-$R^3$, $R^{10}$, $R^{11}$, $R^{12}$-$R^{15}$, Q, W, X, Y, Z, A and the dotted line are as defined above;

b) treating a compound of formula (IV) with a compound of formula (V) in the presence of an appropriate base

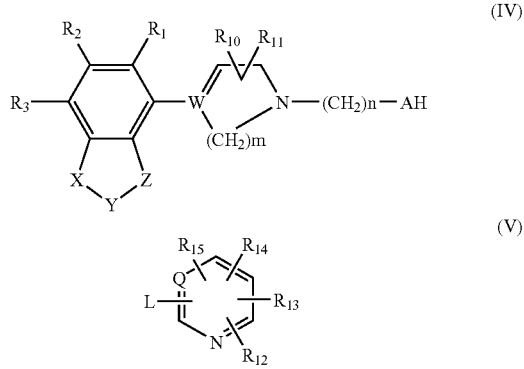

(IV)

(V)

wherein L is a suitable leaving group such as e.g. chloro and n, m, $R^1$-$R^3$, $R^{10}$, $R^{11}$, $R^{12}$-$R^{15}$, Q, W, X, Y, Z, A and the dotted line are as defined above;

Whereupon the compounds of formula (I) are isolated as the free base or in the form of a pharmaceutically acceptable salt thereof.

The reductive amination according to method a) is preferably carried out in an inert organic solvent such as dimethylformamide or tetrahydrofuran in the presence of a reducing agent, eg triacetoxyborohydride, at room temperature.

The arylation according to method b) is conveniently performed in an inert organic solvent such as dimethylformamide in the presence of a base (eg potassium tert-butoxide) at a temperature in the range of 40-100° C., preferably in the range of 40-80° C., and most preferred around 50° C.

Arylpiperazine derivatives of formula (II) are either commercially available or conveniently prepared from the corresponding arylamine according to the method described by Martin et al. *J. Med. Chem.* 1989, 32, 1052, or the method described by Kruse et al. *Rec. Trav. Chim. Pays-Bas* 1988, 107, 303. The staring arylamines are either commercially available or are well-described in the literature.

Aryltetrahydropyridine derivatives of formula (II) are known from literature, cf. U.S. Pat. No. 2,891,066; McElvain et al. *J. Amer. Chem. Soc.* 1959, 72, 3134. Conveniently, the corresponding arylbromide is lithiated with BuLi followed by addition of 1-benzyl-4-piperidone. Subsequent treatment with acid gives the N-benzyl-aryltetrahydropyridine. The benzyl group can be removed by catalytic hydrogenation or by treatment with e.g. ethyl chloroformate to give the corresponding ethyl carbamate followed by acidic or alkaline hydrolysis. The starting arylbromides are either commercially available or well-described in the literature.

Aldehydes of formula (III) are prepared as described in the Examples below. The staring chloropyridines are commercially available or made by methods well-described in the literature The following examples will illustrate the invention further. They are, however, not to be construed as limiting.

EXAMPLES

Melting points were determined on a Büchi SMP-20 apparatus and are uncorrected. Analytical LC-MS data were obtained on a PE Sciex API 150EX instrument equipped with Ionspray source (method D) or heated nebulizer (APCI, methods A and B) and Shimadzu LC-8A/SLC-10A LC system. The LC conditions [30×4.6 mm YMC ODS-A with 3.5 μm particle size] were linear gradient elution with water/acetonitrile/trifluoroacetic acid (90:10:0.05) to water/acetonitrile/trifluoroacetic acid (10:90:0.03) in 4 min at 2 mL/min. Purity was determined by integration of the UV trace (254 nm). The retention times $R_t$ are expressed in minutes.

Mass spectra were obtained by an alternating scan method to give molecular weight information. The molecular ion, MH+, was obtained at low orifice voltage (5-20V) and fragmentation at high orifice voltage (100V).

Preparative LC-MS-separation was performed on the same instrument. The LC conditions (50×20 mm YMC ODS-A with 5 μm particle size) were linear gradient elution with water/acetonitrile/trifluoroacetic acid (80:20:0.05) to water/acetonitrile/trifluoroacetic acid (10:90:0.03) in 7 min at 22.7 mL/min. Fraction collection was performed by split-flow MS detection.

$^1$H NMR spectra were recorded at 500.13 MS on a Bruker Avance DRX500 instrument or at 250.13 MHz on a Bruker AC 250 instrument. Deuterated chloroform (99.8% D) or dimethyl sulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, b=broad singlet. NMR signals corresponding to acidic protons are generally omitted Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography silica gel of type Kieselgel 60, 230-400 mesh ASTM was used. For ion-exchange chromatography (SCX, 1 g, Varian Mega Bond Elut®, Chrompack cat. no. 220776). Prior use the SCX-columns were pre-conditioned with 10% solution of acetic acid in methanol (3 mL).

Example 1

4,6-Dimethyl-2-(2-oxoethylsulfanyl)nicotinonitrile 4,6-Dimethyl-2-mercaptonicotinonitrile (3.0 g) was dissolved in DMF (40 mL) and a solution of potassium tert-butoxide (19.2 mL; 1 M) in tert-butanol added. The mixture was stirred for 10 min, added dropwise to a solution of bromoacetaldehyd dimethylacetal (3.2 g) in DMF (10 ml) and stirred over night at 70° C. The mixture was poured on water and extracted with ethyl acetate, the combined organic phases dried and evaporated to give an oil (5.3 g) which was dissolved in dioxane (40 mL). HCl (20 mL; 3 M) was added and the mixture was stirred at 30° C. for 2 h. $NaHCO_3$ was added until pH reached 5-6, the mixture was extracted with ethyl acetate, the combined organic phases dried with $Na_2SO_4$ and evaporated to give the title compound as an oil (2.9 g). $^1$H NMR ($CDCl_3$): δ 2.45 (s, 6H); 3.35 (d, 2H); 6.85 (s, 1H); 9.55 (t, 1H).

2-{2-[4-(2,3-Dihydrobenzo[1,4]dioxin-5-yl)piperazin-1-yl]ethylsulfanyl}-6-methylnicotinonitrile, 1a 4,6-Dimethyl-2-(2-oxo-ethylsulfanyl)nicotinonitrile (2.9 g) was dissolved in 1,2-dichloroethane (150 mL), a solution of 4-(2,3-dihydrobenzo[1,4]dioxin-5-yl)piperazine (2.6 g) in DMF (150 mL) was added, followed by addition of sodium triacetoxyborohydride (14.9 g) and stirring for 2 h. The mixture was poured on water and $Na_2CO_3$ added until pH reached 7-8. The mixture was extracted with ethyl acetate, the combined organic phases dried and evaporated to give an oil which was subjected to purification by column chromatography (silica gel; ethyl acetate and heptane) giving an oil which precipitated as the oxalate salt (0.36 g) from acetone. LC/MS (m/z) 397 (MH+), RT=1.91, purity: 97%.

The following compounds were prepared analogously:

2-{2-[4-(2,3-Dihydrobenzo[1,4]dioxin-5-yl)piperazin-1-yl]ethylsulfanyl}-6-methyl-4-trifluoromethylnicotinonitrile, 1b LC/MS (m/z) 465 (MH+), RT=2.17, purity: 73%.

2-{2-[4-(8-Cyano-2,3-dihydrobenzo[1,4]dioxin-5-yl) piperazin-1-yl]ethylsulfanyl}-6-methyl-4-trifluoromethylnicotinonitrile, 1c LC/MS (m/z) 490 (MH+), RT=2.21, purity: 82%.

2-{2-[4-(2,3-Dihydrobenzo[1,4]dioxin-5-yl)piperazin-1-yl]ethylsulfanyl}-6-(thiophen-2-yl)-4-trifluoromethylnicotinonitrile, 1d LC/MS (m/z) 533 (MH+), RT=2.38, purity: 86%.

{2-[4-(8-Cyano-2,3-dihydrobenzo[1,4]dioxin-5-yl) piperazin-1-yl]ethylsulfanyl}-6-methylnicotinonitrile, 1e LC/MS (m/z) 422 (MH+), RT=1.95, purity: 98%.

3-{2-[4-(2,3-Dihydrobenzo[1,4]dioxin-5-yl)piperazin-1-yl]ethoxy}-2-methylpyridine, 1f:

LC/MS (m/z) 356 (MH+), RT=1.04, purity: 97%.

2-Chloro-3-{2-[4-(2,3-dihydrobenzo[1,4]dioxin-5-yl)piperazin-1-yl]ethoxy}pyridine, 1g:

LC/MS (m/z) 376 (MH+), RT=1.54, purity: 95%.

2-Bromo-3-{2-[4-(2,3-dihydrobenzo[1,4]dioxin-5-yl)piperazin-1-yl]ethoxy}pyridine, 1h:

LC/MS (m/z) 422 (MH+), RT=1.63, purity: 90%.

3-Chloro-5-{2-[4-(2,3-dihydrobenzo[1,4]dioxin-5-yl)piperazin-1-yl]ethoxy}pyridine, 1i:

LC/MS (m/z) 376 (MH+), RT=1.54, purity: 95%.

2-Chloro-3-{2-[4-(8-cyano-2,3-Dihydrobenzo[1,4] dioxin-5-yl)piperazin-1-yl]ethoxy}pyridine, 1j LC/MS (m/z) 401 (MH+), RT=1.54, purity: 94%.

2-Bromo-3-{2-[4-(8-Cyano-2,3-Dihydrobenzo[1,4] dioxin-5-yl)piperazin-1-yl]ethoxy}pyridine, 1k LCMS (m/z) 445 (MH+), RT=1.63, purity: 92%.

3-Chloro-5-{2-[4-(8-cyano-2,3-dihydrobenzo[1,4] dioxin-5-yl)piperazin-1-yl]ethoxy}pyridine, 1l LC/MS (m/z) 401 (MH+), RT=1.59, purity: 90%.

3-{2-[4-(8-Cyano-2,3-dihydrobenzo[1,4]dioxin-5-yl) piperazin-1-yl]ethoxy}-2-methylpyridine, 1m LC/MS (m/z) 381 (MH+), RT=1.08, purity: 100%.

4-{2-[4-(8-Cyano-2,3-dihydrobenzo[1,4]dioxin-5-yl) piperazin-1-yl]ethylsulfanyl}-3-(piperidin-1-ylsulfonyl)pyridine, 1n LC/MS (m/z) 530 (MH+), purity: 88%.

4-{2-[4-(2,3-Dihydrobenzo[1,4]dioxin-5-yl)piperazin-1-yl]ethylsulfanyl}-3-(piperidin-1-ylsulfonyl) pyridine, 1o LC/MS (m/z) 505 (MH+), RT=1.87, purity: 100%.

2-{4-[4-(2,3-Dihydrobenzo[1,4]dioxin-5-yl)piperazin-1-yl]butylsulfanyl}-5-trifluoromethylpyridine, 1p LC/MS (m/z) 454 (MH+), RT=2.14, purity: 75%.

2-{4-[4-(8-Cyano-2,3-dihydrobenzo[1,4]dioxin-5-yl) piperazin-1-yl]butylsulfanyl}-5-trifluoromethylpyridine, 1q LC/MS (m/z) 479 (MH+), RT=2.14, purity: 82%.

2-{4-[4-(8-Cyano-2,3-dihydrobenzo[1,4]dioxin-5-yl) piperazin-1-yl]butylsulfanyl}-5-trifluoromethylpyridine, 1r LC/MS (m/z) 464 (MH+), RT=2.08, purity: 71%.

2-{3-[4-(2,3-Dihydrobenzo[1,4]dioxin-5-yl)piperazin-1-yl]propylsulfanyl}-5-trifluoromethylpyridine, 1s LC/MS (m/z) 440 (MH+), RT=2.07, purity: 98%.

2-{3-[4-(2,3-Dihydrobenzo[1,4]dioxin-5-yl)piperazin-1-yl]propylsulfanyl}-4,6-dimethylnicotinonitrile, 1t LC/MS (m/z) 425 (MH+), RT=1.99, purity: 100%.

2-{3-[4-(2,3-Dihydrobenzo[1,4]dioxin-5-yl)piperazin-1-yl]butylsulfanyl}-4,6-dimethylnicotinonitrile, 1u LC/MS (m/z) 439 (MH+), RT=2.05, purity: 82%.

2-{3-[4-(8-Cyano-2,3-dihydrobenzo[1,4]dioxin-5-yl) piperazin-1-yl]propylsulfanyl}-5-trifluoromethylpyridine, 1v LC/MS (m/z) 465 (MH+), RT=2.07, purity: 97%.

2-{3-[4-(8-Cyano-2,3-dihydrobenzo[1,4]dioxin-5-yl) piperazin-1-yl]propylsulfanyl}-4,6-dimethylnicotinonitrile, 1x LC/MS (m/z) 450 (MH+), RT=2.00, purity: 98%.

Example 2

2-[4-(2,3-Dihydrobenzo[1,4]dioxin-5-yl)piperazin-1-yl]ethylmercaptane 1-(2,3-Dihydrobenzo[1,4]dioxin-5-yl)piperazine (4.5 g) and thiirane (1.75 g) were dissolved in DMF (200 mL) and refluxed for 1 h. The mixture was evaporated and re-dissolved in THF, dried with $MgSO_4$, filtered and evaporated to give an oil which was subjected to purification by column chromatography (silica gel; ethyl acetate and heptane) giving the title compound as an oil (2.2 g). MS m/z (%): 261 (MH+, 100%), 202 (100%), 159 (23%).

2-{2-[4-(2,3-Dihydrobenzo[3,4]dioxin-5-yl)piperazin-1-yl]ethylsulfanyl}nicotinonitrile, 2a 2-[4-(2,3-Dihydrobenzo[1,4]dioxin-5-yl)piperazin-1-yl]ethylmercaptane (2.2 g) was dissolved in a solution of potassium tert-butoxide (0.81 g) in DMF (25 ml), stirred for 15 min and heated to 50° C. A solution of 2-chloronicotinonitrile (1.91 g) in DMF (25 mL) was added dropwise and stirring was continued for another 2 h at 50° C. The mixture was evaporated and re-dissolved in THF, washed with brine, dried with $MgSO_4$, filtered and evaporated to give an oil which was subjected to purification by column chromatography (silica gel; ethyl acetate, heptane and triethyl amine) giving the title compound as an oil which precipitated as the oxalate salt from acetone. (1.45 g). LC/MS (m/z) 383 (MH+), RT=1.70, purity: 87%.

The following compounds were prepared analogously:

2-{2-[4-(8-Cyano-2,3-dihydrobenzo[1,4]dioxin-5-yl)piperazin-1-yl]ethylsulfanyl}-3-methanesulfonyl-4-methyl-6-phenylpyridine, 2b LC/MS (m/z) 551 (MH+), RT=2.20, purity: 77%.

2-{2-[4-(8-Cyano-2,3-dihydrobenzo[1,4]dioxin-5-yl)piperazin-1-yl]ethylsulfanyl}-4-methyl-6-(piperidin-1-yl)nicotinonitrile, 2c LC/MS (m/z) 505 (MH+), RT=2.33, purity: 87%.

2-{2-[4-(8-Cyano-2,3-Dihydrobenzo[1,4]dioxin-5-yl)piperazin-1-yl]ethylsulfanyl}-6-methylnicotinamide, 2d LC/MS (m/z) 440 (MH+), RT=1.58, purity: 90%.

2-{2-[4-(8-Cyano-2,3-dihydrobenzo[1,4]dioxin-5-yl)piperazin-1-yl]ethylsulfanyl}nicotinonitrile, 2e LC/MS (m/z) 408 (MH+), RT=1.75, purity: 96%.

4-Cyano-2-{2-[4-(2,3-dihydrobenzo[1,4]dioxin-5-yl)piperazin-1-yl]ethoxy}pyridine, 2f:

LC/MS (m/z) 367 (MH+), RT=1.62, purity: 82%.

2-{2-[4-(2,3-Dihydrobenzo[1,4]dioxin-5-yl)piperazin-1-yl]ethoxy}-6-methylnicotinamide, 2g LC/MS (m/z) 399 (MH+), RT=1.55, purity: 97%.

2-{2-[4-(2,3-Dihydrobenzo[1,4]dioxin-5-yl)piperazin-1-yl]ethoxy)-4-methyl-6-(piperidin-1-yl)nicotinonitrile, 2h LC/MS (m/z) 464 (MH+), RT=2.24, purity: 98%.

2-{2-[4-(2,3-Dihydrobenzo[1,4]dioxin-5-yl)piperazin-1-yl]ethoxy)-4-methyl-6-(4-methylpiperazin-1-yl)nicotinonitrile, 2i LC/MS (m/z) 479 (MH+), RT=1.34, purity: 79%.

6-Cyclopropyl-2-{2-[4-(2,3-dihydrobenzo[1,4]dioxin-5-yl)piperazin-1-yl]ethoxy)-4-trifluoromethylnicotinonitrile, 2j LC/MS (m/z) 475 (MH+), RT=2.29, purity: 99%.

2-{2-[4-(2,3-Dihydrobenzo[1,4]dioxin-5-yl)piperazin-1-yl]ethoxy}-3-methanesulfonyl-4-methyl-6-phenylpyridine, 2k LC/MS (m/z) 510 (MH+), RT=2.16, purity: 98%.

2-{3-[4-(2,3-Dihydrobenzo[1,4]dioxin-5-yl)piperazin-1-yl]ethylsulfanyl}-4,6-dimethyl-3-phenylsulfonylpyridine, 2l LC/MS (m/z) 526 (MH+), RT=2.11, purity: 92%.

2-{2-[4-(8-Cyano-2,3-dihydrobenzo[1,4]dioxin-5-yl)piperazin-1-yl]ethylsulfanyl}pyridine, 2m LC/MS (m/z) 383 (MH+), RT=1.67, purity: 87%.

2-{3-[4-(2,3-Dihydrobenzo[1,4]dioxin-5-yl)piperazin-1-yl]ethylsulfanyl}-4,6-dimethylnicotinonitrile, 2n LC/MS (m/z) 412 (MH+), RT=2.02, purity: 96%.

6-Chloro-2-{3-[4-(2,3-dihydrobenzo[1,4]dioxin-5-yl)piperazin-1-yl]ethylsulfanyl}-4-methylnicotinonitrile, 2o LC/MS (m/z) 432 (MH+), RT=2.00, purity: 93%.

5-Chloro-2-{3-[4-(2,3-dihydrobenzo[1,4]dioxin-5-yl)piperazin-1-yl]ethylsulfanyl}nicotinonitrile, 2p LC/MS (m/z) 418 (MH+), RT=1.90, purity: 73%.

6-Chloro-2-{3-[4-(2,3-dihydrobenzo[1,4]dioxin-5-yl)piperazin-1-yl]ethylsulfanyl}nicotinonitrile, 2q LC/MS (m/z) 418 (MH+), RT=1.91, purity: 72%.

6-Chloro-2-{3-[4-(2,3-dihydrobenzo[1,4]dioxin-5-yl)piperazin-1-yl]ethylsulfanyl}-5-fluoronicotinonitrile, 2r LC/MS (m/z) 436 (MH+), RT=1.95, purity: 89%.

2-{3-[4-(8-Cyano-2,3-dihydrobenzo[1,4]dioxin-5-yl)piperazin-1-yl]ethylsulfanyl}-4,6-dimethylnicotinonitrile, 2s LC/MS (m/z) 436 (MH+), RT=2.04, purity: 78%.

6-Chloro-2-{3-[4-(8-cyano-2,3-dihydrobenzo[1,4]dioxin-5-yl)piperazin-1-yl]ethylsulfanyl}-4-methylnicotinonitrile, 2t LC/MS (m/z) 457 (MH+), RT=2.04, purity: 87%.

5-Chloro-2-{3-[4-(8-cyano-2,3-dihydrobenzo[1,4]dioxin-5-yl)piperazin-1-yl]ethylsulfanyl}-4,6-dimethylnicotinonitrile, 2u LC/MS (m/z) 471 (MH+), RT=2.24, purity: 81%.

5-Chloro-2-{3-[4-(8-cyano-2,3-dihydrobenzo[1,4]dioxin-5-yl)piperazin-1-yl]ethylsulfanyl}nicotinonitrile, 2v LC/MS (m/z) 443 (MH+), RT=1.97, purity: 81%.

6-Chloro-2-{3-[4-(8-cyano-2,3-dihydrobenzo[1,4]dioxin-5-yl)piperazin-1-yl]ethylsulfanyl}nicotinonitrile, 2x LC/MS (m/z) 443 (MH+), RT=1.91 purity: 87%.

6-Chloro-2-{3-[4-(8-cyano-2,3-dihydrobenzo[1,4]dioxin-5-yl)piperazin-1-yl]ethylsulfanyl}-5-fluoronicotinonitrile, 2y LC/MS (m/z) 461 (MH+), RT=1.62, purity: 84%.

2-[2-[4-(6-Chloro-2,3-dihydro-1,4-benzoxazin-3-on-8-yl)piperazin-1-yl]ethylsulfanyl]nicotinonitrile, 2z LC/MS (m/z) 431 (MH+), RT=1.62, purity: 94%.

2-[2-[4-(6-Chloro-2,3-dihydro-1,4-benzoxazin-3-on-8-yl)piperazin-1-yl]ethylsulfanyl]-4,6-dimethylnicotinonitrile, 2aa LC/MS (m/z) 459 (MH+), RT=1.87, purity: 72%.

6-Chloro-2-[2-[4-(6-chloro-2,3-dihydro-1,4-benzoxazin-3-on-8-yl)piperazin-1-yl]ethylsulfanyl]-4-methylnicotinonitrile, 2ab LC/MS (m/z) 479 (MH+), RT=1.91, purity: 97%.

4-Chloro-2-[2-[4-(6-chloro-2,3-dihydro-1,4-benzoxazin-3-on-8-yl)piperazin-1-yl]ethylsulfanyl]-6-methylnicotinonitrile, 2ac LC/MS (m/z) 479 (MH+), RT=1.87, purity: 85%.

5-Chloro-2-[2-[4-(6-chloro-2,3-dihydro-1,4-benzoxazin-3 on-8-yl)piperazin-1-yl]ethylsulfanyl]-4,6-dimethylnicotinonitrile, 2ad LC/MS (m/z) 493 (MH+), RT=2.12, purity: 98%.

5-Chloro-2-[2-[4-(6-chloro-2,3-dihydro-1,4-benzoxazin-3-on-8-yl)piperazin-1-yl]ethylsulfanyl]nicotinonitrile, 2ae LC/MS (m/z) 465 (MH+), RT=1.87, purity: 96%.

6-Chloro-2-[2-[4-(6-chloro-2,3-dihydro-1,4-benzoxazin-3-on-8-yl)piperazin-1-yl]ethylsulfanyl]nicotinonitrile, 2af LC/MS (m/z) 465 (MH+), RT=1.79, purity: 98%.

6-Chloro-2-[2-[4-(6-chloro-2,3-dihydro-1,4-benzoxazin-3-on-8-yl)piperazin-1-yl]ethylsulfanyl]-5-fluoronicotinonitrile, 2ag LC/MS (m/z) 483 (MH+), RT=1.83, purity: 96%.

2-[2-[4-(6-Chloro-2,3-dihydro-1,4-benzoxazin-8-yl)piperazin-1-yl]ethylsulfanyl]nicotinonitrile, 2ah LC/MS (m/z) 417 (MH+), RT=1.75, purity: 93%.

2-[2-[4-(6-Chloro-2,3-dihydro-1,4-benzoxazin-8-yl)piperazin-1-yl]ethylsulfanyl]-4,6-dimethylnicotinonitrile, 2ai LC/MS (m/z) 445 (MH+), RT=2.04, purity: 96%.

6-Chloro-2-[2-[4-(6-chloro-2,3-dihydro-1,4-benzoxazin-8-yl)piperazin-1-yl]ethylsulfanyl]-4-methylnicotinonitrile, 2aj LC/MS (m/z) 465 (MH+), RT=2.08, purity: 96%.

4-Chloro-2-[2-[4-(6-chloro-2,3-dihydro-1,4-benzoxazin-8-yl)piperazin-1-yl]ethylsulfanyl]-6-methylnicotinonitrile, 2ak LC/MS (m/z) 465 (MH+), RT=1.95, purity: 89%.

5-Chloro-2-[2-[4-(chloro-2,3-dihydro-1,4-benzoxazin-8-yl)piperazin-1-yl]ethylsulfanyl]-4,6-dimethylnicotinonitrile, 2al LC/MS (m/z) 479 (MH+), RT=2.24, purity: 97%.

5-Chloro-2-[2-[4-(6-chloro-2,3-dihydro-1,4-benzoxazin-8-yl)piperazin-1-yl]ethylsulfanyl]nicotinonitrile, 2am LC/MS (m/z) 451 (MH+), RT=2.00, purity: 96%.

6-Chloro-2-[2-[4-(6-chloro-2,3-dihydro-1,4-benzoxazin-8-yl)piperazin-1-yl]ethylsulfanyl]nicotinonitrile, 2an LC/MS (m/z) 451 (MH+), RT=1.95, purity: 74%.

6-Chloro-2-[2-[4-(6-chloro-2,3-dihydro-1,4-benzoxazin-8-yl)piperazin-1-yl]ethylsulfanyl]-5-fluoronicotinonitrile, 2ao LC/MS (m/z) 469 (MH+), RT=2.00, purity: 96%.

5-Cyano-4-{2-[4-(2,3-dihydrobenzo[1,4]dioxin-5-yl)piperazin-1-yl]ethylsulfanyl}pyrimidine, 2ap LC/MS (m/z) 384 (MH+), RT=1.66, purity: 99%.

5-Cyano-4-{2-[4-(2,3-dihydrobenzo[1,4]dioxin-5-yl) piperazin-1-yl]ethylsulfanyl}-6-methylsulfanyl-2-phenylpyrimidine, 2aq LC/MS (m/z) 507 (MH+), RT=2.49, purity: 93%.

5-Cyano-4-{2-[4-(8-cyano-2,3-dihydrobenzo[1,4] dioxin-5-yl)piperazin-1-yl]ethylsulfanyl}pyrimidine, 2ar LC/MS (m/z) 409 (MH+), RT=1.70, purity: 98%.

5-Cyano-4-{2-[4-(8-cyano-2,3-dihydrobenzo[1,4] dioxin-5-yl)piperazin-1-yl]ethylsulfanyl}-6-methylsulfanyl-2-phenylpyrimidine, 2 as LC/MS (m/z) 532 (MH+), RT=2.49, purity: 91%.

2-{2-[4-(2,3-Dihydrobenzo[1,4]dioxin-5-yl)piperazin-1-yl]ethylsulfanyl}-4,6-dimethylpyrimidine, 2at LC/MS (m/z) 387 (MH+), RT=1.66, purity: 95%.

2-{2-[4-(8-Cyano-2,3-dihydrobenzo[1,4]dioxin-5-yl) piperazin-1-yl]ethylsulfanyl}-4,6-dimethylpyrimidine, 2au LC/MS (m/z) 413 (MH+), RT=1.70, purity: 80%.

2-{2-[4-(2,3-Dihydrobenzo[1,4]dioxin-5-yl)piperazin-1-yl]ethylsulfanyl}-4-methoxynicotinonitrile: 2av LC/MS (m/z) 414 (MH+), RT=1.8, purity: 83%.

6-Chloro-2-{2-[4-(2,3-dihydrobenzo[1,4]dioxin-5-yl)piperazin-1-yl]ethylsulfanyl}-5-fluoronicotinonitrile, 2ax LC/MS (m/z) 436 (MH+), RT=2.0, purity: 86%.

6-Chloro-2-{2-[4-(8-cyano-2,3-dihydrobenzo[1,4] dioxin-5-yl)piperazin-1-yl]ethylsulfanyl}-5-fluoronicotinonitrile, 2ay LC/MS (m/z) 461 (MH+), RT=2.0, purity: 84%.

2-{2-[4-(2,3-Dihydrobenzo[1,4]dioxin-5-yl)piperazin-1-yl]ethylsulfanyl}-5-ethylpyrimidine, 2az LC/MS (m/z) 387 (MH+), RT=1.8, purity: 83%.

2-{2-[4-(2,3-Dihydrobenzo[1,4]dioxin-5-yl)piperazin-1-yl]ethylsulfanyl}-4-trifluoromethylpyrimidine, 2ba LC/MS (m/z) 427 (MH+), RT=1.8, purity: 78%.

2-{2-[4-(2,3-Dihydrobenzo[1,4]dioxin-5-yl)piperazin-1-yl]ethylsulfanyl}-4,6-dimethoxypyrimidine, 2bb LC/MS (m/z) 420 (MH+), RT=1.9, purity: 70%.

4-Chloro-2-{2-[4-(8-cyano-2,3-dihydrobenzo[1,4] dioxin-5-yl)piperazin-1-yl]ethylsulfanyl}-6-methylpyrimidine, 2bc LC/MS (m/z) 433 (MH+), RT=1.8, purity: 78%.

2-{2-[4-(8-Cyano-2,3-dihydrobenzo[1,4]dioxin-5-yl) piperazin-1-yl]ethylsulfanyl}-4-trifluoromethylpyrimidine, 2bd LC/MS (m/z) 434 (MH+), RT=2.0, purity: 84%.

Pharmacological Testing

The affinity of the compounds of the invention to $5\text{-HT}_{1A}$ receptors was determined by measuring the inhibition of binding of a radioactive ligand at $5\text{-HT}_{1A}$ receptors as described in the following test:

Inhibition of $^3$H-5-CT Binding to Human $5\text{-HT}_{1A}$ Receptors.

By this method the inhibition by drugs of the binding of the $5\text{-HT}_{1A}$ agonist $^3$H-5-carboxamido tryptamine ($^3$H-5-CT) to cloned human $5\text{-HT}_{1A}$ receptors stably expressed in transfected HeLa cells (HA7) (Fargin, A. et al. *J. Biol. Chem.* 1989, 264, 14848) is determined in vitro. The assay was performed as a modification of the method described by Harrington, M. A. et al. *J. Pharmacol. Exp. Ther.* 1994, 268, 1098. Human $5\text{-HT}_{1A}$ receptors (40 μg of cell homogenate) were incubated for 15 minutes at 37° C. in 50 mM Tris buffer at pH 7.7 in the presence of $^3$H-5-CT. Non-specific binding was determined by including 10 μM of metergoline. The reaction was terminated by rapid filtration through Unifilter GF/B filters on a Tomtec Cell Harvester. Filters were counted in a Packard Top Counter. Compounds 1a, 1b, 2a, 2c, 2l, 2o, 2s, 2u, 2z, 2aa, 2ah, 2ai and 2aj were tested and showed $IC_{50}$ values of less than 300 nM.

The compounds of the invention have also been tested for their effect on re-uptake of serotonin in the following test:

Inhibition of $^3$H-5-HT Uptake into Rat Brain Synaptosomes.

Using this method, the ability of drugs to inhibit the accumulation of $^3$H-5-HT into whole rat brain synaptosomes is determined in vitro. The assay was performed as described by Hyttel, J. *Psychopharmacology* 1978, 60, 13. Compounds 1a, 1r, 2a, 2c, 2l, 2o, 2s, 2u, 2z, 2aa, 2ah, 2ai and 2aj were tested and showed $IC_{50}$ values of less than 20 nM.

The $5\text{-HT}_{1A}$ antagonistic activity of some of the compounds of the invention has been estimated in vitro at cloned $5\text{-HT}_{1A}$ receptors stably expressed in transfected HeLa cells (HA7). In this test, $5\text{-HT}_{1A}$ antagonistic activity is estimated by measuring the ability of the compounds to antagonize the 5-HT induced inhibition of forskolin induced cAMP accumulation. The assay was performed as a modification of the method described by Pauwels, P. J. et al. *Biochem. Pharmacol.* 1993, 45, 375. Compounds 1a, 1b, 1e and 1v were tested and showed $IC_{50}$ values of less than 7000 nM.

Some of the compounds of the invention have also been tested for their in vivo effect on $5\text{-HT}_{1A}$ receptors in the assay described by Sánchez. C. et al. *Eur. J. Pharmacol.* 1996, 315, pp 245. In this test, antagonistic effects of test compounds are determined by measuring the ability of the test compounds to inhibit 5-MeO-DMT induced 5-HT syndrome.

The compounds of the present invention possess valuable activity as serotonin re-uptake inhibitors and have antagonistic effect at $5\text{-HT}_{1A}$ receptors. The compounds of the invention are therefore considered useful for the treatment of diseases and disorders responsive to the inhibition of serotonin re-uptake and antagonistic activity at $5\text{-H}_{1A}$ receptors. Diseases responsive to the inhibition of serotonin re-uptake are well-known in the art and include affective disorders, such as depression, psychosis, anxiety disorders including general anxiety disorder, panic disorder, obsessive compulsive disorder, etc.

As explained above, the antagonistic activity at $5-HT_{1A}$ receptors of the compounds of the invention will counteract the negative feed back mechanism induced by the inhibition of serotonin reuptake and is thereby expected to improve the effect of the serotonin reuptake inhibiting activity of the compounds of the invention.

The compounds as claimed herein are therefore considered to be particularly useful as fast onset of action medicaments for the treatment of depression. The compounds may also be useful for the treatment of depressions which are non-responsive to currently available SSRIs.

Some of the compounds of the invention have also been found to have affinity to dopamine $D_3$ and $D_4$ receptors in the following two assays.

Inhibition of the Binding of $^3$H-YM-09151-2 to Human Dopamine $D_4$ Receptors

By this method, the inhibition by drugs of the binding of [$^3$H]YM-09151-2 (0.06 nM) to membranes of human cloned dopamine $D_{4,2}$-receptors expressed in CHO-cells is determined in vitro. Method modified from NEN Life Science Products, Inc., technical data certificate PC2533-10/96.

Inhibition of the Binding of [$^3$H]-Spiperone to Human $D_3$ Receptors

By this method, the inhibition by drugs of the binding [$^3$]Spiperone (0.3 nM) to membranes of human cloned dopamine $D_3$-receptors expressed in CHO-cells is determined in vitro. Method modified from R. G. MacKenzie et al. *Eur. J. Pharm.-Mol. Pharm. Sec.* 1994, 266, 79-85.

As seen from the above, the compounds of the invention show affinity for the $5-HT_{1A}$ receptors, inhibitory activity at serotonin reuptake sites, and affinity for dopamine $D_3$ and $D_4$ receptors. Accordingly, the compounds are considered useful for the treatment of psychiatric and neurological disorders as mentioned previously.

Pharmaceutical Formulation

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients. Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well-known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 1000 mg. The total daily dose is usually in the range of about 0.05-500 mg, and most preferably about 0.1 to 50 mg of the active compound of the invention.

The invention claimed is:

1. A compound of Formula I

[Chemical structure of Formula I]

wherein

X represents O or $NR^{16}$;

Y is $-CR^6R^7-$, $-CR^6R^7-CR^8R^9-$, or $CO-CR^6R^7$;

Z represents O;

n is 2, 3, 4, 5, 6, 7, 8, 9 or 10;

m is 2;

A is O or S;

W is N;

Q is N, C or CH;

$R^1-R^3$ and $R^6-R^9$ are each independently selected from hydrogen, halogen, nitro, cyano, trifluoromethyl, trifluoromethoxy, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, formyl, and acyl; and $R^{16}$ is selected from hydrogen, $C_{1-6}$-alkyl, $C_{3-8}$-cycloalkyl, $C_{3-8}$-cycloalkyl-$C_{1-6}$-alkyl, formyl, and acyl; and $R^{10}$ and $R^{11}$ are each independently selected from hydrogen and $C_{1-6}$-alkyl; and $R^{12}$, $R^{13}$, $R^{14}$ and $R^{15}$ are each independently selected from hydrogen, halogen, nitro, cyano, trifluoromethyl, trifluoromethoxy, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, heteroaryl, $C_{1-6}$-alkoxy, $C_{1-6}$-alkylthio, $C_{1-6}$-alkylsulphonyl, hydroxy, formyl, acyl, amino, acylamino, aminocarbonyl, $C_{1-6}$-alkoxycarbonylamino, aminocarbonylamino, $C_{1-6}$-alkylaminocarbonylamino, di($C_{1-6}$-alkyl)aminocarbonylamino, $SO_2NR^{20}R^{21}$ and $NR^{20}R^{21}$ wherein $R^{20}$ and $R^{21}$ independently represent hydrogen, $C_{1-6}$-alkyl, $C_{3-8}$-cycloalkyl or phenyl; or $R^{20}$ and $R^{21}$ together with the nitrogen to which they are attached form a piperidine;

any of its enantiomers or any mixture thereof, or a pharmaceutically acceptable acid addition salt thereof.

2. The compound of claim 1, wherein Y is $-CR^6R^7$ or Y is $CO-CR^6R^7$.

3. The compound of claim 1, wherein X is O or NH.

4. The compound of claim 1, wherein n is 2, 3 or 4.

5. The compound of claim 4, wherein n is 2.

6. The compound of claim 1, wherein $R^1$, $R^2$ and $R^3$ are independently hydrogen, halogen or cyano.

7. The compound of claim 1, wherein $R^{12}$, $R^{13}$, $R^{14}$ and $R^{15}$ are independently selected from the group consisting of hydrogen, halogen, $C_{1-6}$-alkyl, $C_{2-6}$-alkenyl, $C_{1-6}$-alkoxy, cyano, $C_{1-6}$-alkylsulphonyl, acyl, nitro, trifluoromethyl and trifluoromethoxy.

8. The compound of claim 1, wherein $R^{12}$, $R^{13}$, $R^{14}$ and $R^{15}$ are independently selected from a group consisting of hydrogen, heteroaryl, trifluoromethyl, cyano, $C_{1-6}$-alkyl, $C_{3-8}$-cycloalkyl, halogen, NR$^{20}$R$^{21}$, SO$_2$NR$^{20}$R$^{21}$, aryl, C$_{1-6}$-alkyl-sulfonyl aminocarbonyl and acylamino.

9. The compound of claim 8, wherein R$^{12}$, R$^{13}$, R$^{14}$ and R$^{15}$ are independently selected from the group consisting of hydrogen, thienyl, trifluoromethyl, cyano, methyl, ethyl, cyclopropyl, chloro, bromo, fluoro, piperazinyl, 1-piperidinyl, 1-piperidinyl-sulfonyl, methanesulfonyl, methylsulfidyl, phenyl aminocarbonyl and acylamino.

10. A compound selected from the group consisting of:
2-{2-[4-(2,3-Dihydrobenzo[1,4]dioxin-5-yl)piperazin-1-yl]ethylsulfanyl}-6-methylnicotinonitrile,
2-{2-[4-(2,3-Dihydrobenzo[1,4]dioxin-5-yl)piperazin-1-yl]ethylsulfanyl}-6-methyl-4-trifluoromethylnicotinonitrile,
2-{2-[4-(8-Cyano-2,3-dihydrobenzo[1,4]dioxin-5-yl)piperazin-1-yl]ethylsulfanyl}-6-methyl-4-trifluoromethylnicotinonitrile,
2-{2-[4-(2,3-Dihydrobenzo[1,4]dioxin-5-yl)piperazin-1-yl]ethylsulfanyl}-6-(thiophen-2-yl)-4-trifluoromethylnicotinonitrile,
{2-[4-(8-Cyano-2,3-dihydrobenzo[1,4]dioxin-5-yl)piperazin-1-yl]ethylsulfanyl}-6-methylnicotinonitrile,
3-{2-[4-(2,3-Dihydrobenzo[1,4]dioxin-5-yl)piperazin-1-yl]ethoxy}-2-methylpyridine,
2-Chloro-3-{2-[4-(2,3-dihydrobenzo[1,4]dioxin-5-yl)piperazin-1-yl]ethoxy}pyridine,
2-Bromo-3-{2-[4-(2,3-dihydrobenzo[1,4]dioxin-5-yl)piperazin-1-yl]ethoxy}pyridine,
3-Chloro-5-{2-[4-(2,3-dihydrobenzo[1,4]dioxin-5-yl)piperazin-1-yl]ethoxy}pyridine,
2-Chloro-3-{2-[4-(8-cyano-2,3-Dihydrobenzo[1,4]dioxin-5-yl)piperazin-1-yl]ethoxy}pyridine,
2-Bromo-3-{2-[4-(8-Cyano-2,3-Dihydrobenzo[1,4]dioxin-5-yl)piperazin-1-yl]ethoxy}pyridine,
3-Chloro-5-{2-[4-(8-cyano-2,3-dihydrobenzo[1,4]dioxin-5-yl)piperazin-1-yl]ethoxy}pyridine,
3-{2-[4-(8-Cyano-2,3-dihydrobenzo[1,4]dioxin-5-yl)piperazin-1-yl]ethoxy}-2-methylpyridine,
4-{2-[4-(8-Cyano-2,3-dihydrobenzo[1,4]dioxin-5-yl)piperazin-1-yl]ethylsulfanyl}-3-(piperidin-1-ylsulfonyl)pyridine,
4-{2-[4-(2,3-Dihydrobenzo[1,4]dioxin-5-yl)piperazin-1-yl]ethylsulfanyl}-3-(piperidin-1-ylsulfonyl)pyridine,
2-{4-[4-(2,3-Dihydrobenzo[1,4]dioxin-5-yl)piperazin-1-yl]butylsulfanyl}-5-trifluoromethylpyridine,
2-{4-[4-(8-Cyano-2,3-dihydrobenzo[1,4]dioxin-5-yl)piperazin-1-yl]butylsulfanyl}-5-trifluoromethylpyridine,
2-{4-[4-(8-Cyano-2,3-dihydrobenzo[1,4]dioxin-5-yl)piperazin-1-yl]butylsulfanyl}-5-trifluoromethylpyridine,
2-{3-[4-(2,3-Dihydrobenzo[1,4]dioxin-5-yl)piperazin-1-yl]propylsulfanyl}-5-trifluoromethylpyridine,
2-{3-[4-(2,3-Dihydrobenzo[1,4]dioxin-5-yl)piperazin-1-yl]propylsulfanyl}-4,6-dimethyl-nicotinonitrile,
2-{3-[4-(2,3-Dihydrobenzo[1,4]dioxin-5-yl)piperazin-1-yl]butylsulfanyl}-4,6-dimethyl-nicotinonitrile,
2-{3-[4-(8-Cyano-2,3-dihydrobenzo[1,4]dioxin-5-yl)piperazin-1-yl]propylsulfanyl}-5-trifluoromethylpyridine,
2-{3-[4-(8-Cyano-2,3-dihydrobenzo[1,4]dioxin-5-yl)piperazin-1-yl]propylsulfanyl}-4,6-dimethylnicotinonitrile,
2-{2-[4-(2,3-Dihydrobenzo[1,4]dioxin-5-yl)piperazin-1-yl]ethylsulfanyl}nicotinonitrile,
2-{2-[4-(8-Cyano-2,3-dihydrobenzo[1,4]dioxin-5-yl)piperazin-1-yl]ethylsulfanyl}-3-methanesulfonyl-4-methyl-6-phenylpyridine,
2-{2-[4-(8-Cyano-2,3-dihydrobenzo[1,4]dioxin-5-yl)piperazin-1-yl]ethylsulfanyl}-4-methyl-6-(piperidin-1-yl)nicotinonitrile,
2-{2-[4-(8-Cyano-2,3-Dihydrobenzo[1,4]dioxin-5-yl)piperazin-1-yl]ethylsulfanyl}-6-methylnicotinamide,
2-{2-[4-(8-Cyano-2,3-dihydrobenzo[1,4]dioxin-5-yl)piperazin-1-yl]ethylsulfanyl}nicotinonitrile,
4-Cyano-2-{2-[4-(2,3-dihydrobenzo[1,4]dioxin-5-yl)piperazin-1-yl]ethoxy}pyridine,
2-{2-[4-(2,3-Dihydrobenzo[1,4]dioxin-5-yl)piperazin-1-yl]ethoxy}-6-methylnicotinamide,
2-{2-[4-(2,3-Dihydrobenzo[1,4]dioxin-5-yl)piperazin-1-yl]ethoxy)-4-methyl-6-(piperidin-1-yl)nicotinonitrile,
2-{2-[4-(2,3-Dihydrobenzo[1,4]dioxin-5-yl)piperazin-1-yl]ethoxy)-4-methyl-6-(4-methylpiperazin-1-yl)nicotinonitrile,
6-Cyclopropyl-2-{2-[4-(2,3-dihydrobenzo[1,4]dioxin-5-yl)piperazin-1-yl]ethoxy)-4-trifluoromethylnicotinonitrile,
2-{2-[4-(2,3-Dihydrobenzo[1,4]dioxin-5-yl)piperazin-1-yl]ethoxy}-3-methanesulfonyl-4-methyl-6-phenylpyridine,
2-{3-[4-(2,3-Dihydrobenzo[1,4]dioxin-5-yl)piperazin-1-yl]ethylsulfanyl}-4,6-dimethyl-3-phenylsulfonylpyridine,
2-{2-[4-(8-Cyano-2,3-dihydrobenzo[1,4]dioxin-5-yl)piperazin-1-yl]ethylsulfanyl}pyridine,
2-{3-[4-(2,3-Dihydrobenzo[1,4]dioxin-5-yl)piperazin-1-yl]ethylsulfanyl}-4,6-dimethylnicotinonitrile,
6-Chloro-2-{3-[4-(2,3-dihydrobenzo[1,4]dioxin-5-yl)piperazin-1-yl]ethylsulfanyl}-4-methylnicotinonitrile,
5-Chloro-2-{3-[4-(2,3-dihydrobenzo[1,4]dioxin-5-yl)piperazin-1-yl]ethylsulfanyl}nicotinonitrile,
6-Chloro-2-{3-[4-(2,3-dihydrobenzo[1,4]dioxin-5-yl)piperazin-1-yl]ethylsulfanyl}nicotinonitrile,
6-Chloro-2-{3-[4-(2,3-dihydrobenzo[1,4]dioxin-5-yl)piperazin-1-yl]ethylsulfanyl}-5-fluoronicotinonitrile,
2-{3-[4-(8-Cyano-2,3-dihydrobenzo[1,4]dioxin-5-yl)piperazin-1-yl]ethylsulfanyl}-4,6-dimethylnicotinonitrile,
6-Chloro-2-{3-[4-(8-cyano-2,3-dihydrobenzo[1,4]dioxin-5-yl)piperazin-1-yl]ethylsulfanyl}-4-methylnicotinonitrile,
5-Chloro-2-{3-[4-(8-cyano-2,3-dihydrobenzo[1,4]dioxin-5-yl)piperazin-1-yl]ethylsulfanyl}-4,6-dimethylnicotinonitrile,
5-Chloro-2-{3-[4-(8-cyano-2,3-dihydrobenzo[1,4]dioxin-5-yl)piperazin-1-yl]ethylsulfanyl}nicotinonitrile,
6-Chloro-2-{3-[4-(8-cyano-2,3-dihydrobenzo[1,4]dioxin-5-yl)piperazin-1-yl]ethylsulfanyl}nicotinonitrile,
6-Chloro-2-{3-[4-(8-cyano-2,3-dihydrobenzo[1,4]dioxin-5-yl)piperazin-1-yl]ethylsulfanyl}-5-fluoronicotinonitrile,
2-[2-[4-(6-Chloro-2,3-dihydro-1,4-benzoxazin-3-on-8-yl)piperazin-1-yl]ethylsulfanyl]nicotinonitrile,
2-[2-[4-(6-Chloro-2,3-dihydro-1,4-benzoxazin-3-on-8-yl)piperazin-1-yl]ethylsulfanyl]-4,6-dimethylnicotinonitrile,
6-Chloro-2-[2-[4-(6-chloro-2,3-dihydro-1,4-benzoxazin-3-on-8-yl)piperazin-1-yl]ethylsulfanyl]-4-methylnicotinonitrile,
4-Chloro-2-[2-[4-(6-chloro-2,3-dihydro-1,4-benzoxazin-3-on-8-yl)piperazin-1-yl]ethylsulfanyl]-6-methylnicotinonitrile,
5-Chloro-2-[2-[4-(6-chloro-2,3-dihydro-1,4-benzoxazin-3-on-8-yl)piperazin-1-yl]ethylsulfanyl]-4,6-dimethylnicotinonitrile, 5-Chloro-2-[2-[4-(6-chloro-2,3-dihydro-1,4-benzoxazin-3-on-8-yl)piperazin-1-yl]ethylsulfanyl]nicotinonitrile, 6-Chloro-2-[2-[4-(6-chloro-2,3-dihydro-1,4-benzoxazin-3-on-8-yl)piperazin-1-yl]ethylsulfanyl]nicotinonitrile, 6-Chloro-2-[2-[4-(6-chloro-2,3-dihydro-1,4-benzoxazin-3-on-8-yl)piperazin-1-yl]ethylsulfanyl]-5-fluoronicotinonitrile, 2-[2-[4-(6-Chloro-2,3-dihydro-1,4-benzoxazin-8-yl)piperazin-1-yl]ethylsulfanyl]nicotinonitrile, 2-[2-[4-(6-Chloro-2,3-dihydro-1,4-benzoxazin-8-yl)piperazin-1-yl]ethylsulfanyl]-4,6-dimethylnicotinonitrile, 6-Chloro-2-[2-[4-(6-chloro-2,3-dihydro-1,4-benzoxazin-8-yl)piperazin-1-yl]ethylsulfanyl]-4-methylnicotinonitrile, 4-Chloro-2-[2-[4-(6-chloro-2,3-dihydro-1,4-benzoxazin-8-yl)piperazin-1-yl]ethylsulfanyl]-6-methylnicotinonitrile, 5-Chloro-2-[2-[4-(6-chloro-2,3-dihydro-1,4-benzoxazin-8-yl)piperazin-1-yl]ethylsulfanyl]-4,6-dimethylnicotinonitrile, 5-Chloro-2-[2-[4-(6-chloro-2,3-dihydro-1,4-benzoxazin-8-yl)piperazin-1-yl]ethylsulfanyl]nicotinonitrile, 6-Chloro-2-[2-[4-(6-chloro-2,3-dihydro-1,4-benzoxazin-8-yl)piperazin-1-yl]ethylsulfanyl]nicotinonitrile, 6-Chloro-2-[2-[4-(6-chloro-2,3-dihydro-1,4-benzoxazin-8-yl)piperazin-1-yl]ethylsulfanyl]-5-fluoronicotinonitrile, 5-Cyano-4-{2-[4-(2,3-dihydrobenzo[1,4]dioxin-5-yl)piperazin-1-yl]ethylsulfanyl}pyrimidine, 5-Cyano-4-{2-[4-(2,3-dihydrobenzo[1,4]dioxin-5-yl)piperazin-1-yl]ethylsulfanyl}-6-methylsulfanyl-2-phenylpyrimidine, 5-Cyano-4-{2-[4-(8-cyano-2,3-dihydrobenzo[1,4]dioxin-5-yl)piperazin-1-yl]ethylsulfanyl}pyrimidine, 5-Cyano-4-{2-[4-(8-cyano-2,3-dihydrobenzo[1,4]dioxin-5-yl)piperazin-1-yl]ethylsulfanyl}-6-methylsulfanyl-2-phenylpyrimidine, 2-{2-[4-(2,3-Dihydrobenzo[1,4]dioxin-5-yl)piperazin-1-yl]ethylsulfanyl}-4,6-dimethylpyrimidine, 2-{2-[4-(8-Cyano-2,3-dihydrobenzo[1,4]dioxin-5-yl)piperazin-1-yl]ethylsulfanyl}-4,6-dimethylpyrimidine, 2-{2-[4-(2,3-Dihydrobenzo[1,4]dioxin-5-yl)piperazin-1-yl]ethylsulfanyl}-4-methoxynicotinonitrile, 6-Chloro-2-{2-[4-(2,3-dihydrobenzo[1,4]dioxin-5-yl)piperazin-1-yl]ethylsulfanyl}-5-fluoronicotinonitrile, 6-Chloro-2-{2-[4-(8-cyano-2,3-dihydrobenzo[1,4]dioxin-5-yl)piperazin-1-yl]ethylsulfanyl}-5-fluoronicotinonitrile, 2-{2-[4-(2,3-Dihydrobenzo[1,4]dioxin-5-yl)piperazin-1-yl]ethylsulfanyl}-5-ethylpyrimidine, 2-{2-[4-(2,3-Dihydrobenzo[1,4]dioxin-5-yl)piperazin-1-yl]ethylsulfanyl}-4-trifluoromethylpyrimidine, 2-{2-[4-(2,3-Dihydrobenzo[1,4]dioxin-5-yl)piperazin-1-yl]ethylsulfanyl}-4,6-dimethoxypyrimidine, 4-Chloro-2-{2-[4-(8-cyano-2,3-dihydrobenzo[1,4]dioxin-5-yl)piperazin-1-yl]ethylsulfanyl}-6-methylpyrimidine, and 2-{2-[4-(8-Cyano-2,3-dihydrobenzo[1,4]dioxin-5-yl)piperazin-1-yl]ethylsulfanyl}-4-trifluoromethylpyrimidine;

or a pharmaceutically acceptable acid addition salt thereof.

11. A pharmaceutical composition comprising at least one compound of Formula I according to claim 1, or a pharmaceutically acceptable acid addition salt thereof in a therapeutically effective amount and in combination with one or more pharmaceutically acceptable carriers or diluents.

12. A method for the treatment of a disorder or disease of living animal body selected from the group consisting of affective disorder and psychosis, comprising administering to such living animal body a therapeutically effective amount of a compound according to claim 1 or a pharmaceutically acceptable acid addition salt thereof.

13. A method for the treatment of a disorder or disease of living animal body selected from the group consisting of affective disorder and psychosis, comprising administering to such living animal body a therapeutically effective amount of a compound according to claim 10 or a pharmaceutically acceptable acid addition salt thereof.

14. The method of treatment according to claim 12 wherein the affective disorder is selected from the group consisting of general anxiety disorder, panic disorder, obsessive disorder, depression and social phobia.

15. The method of treatment according to claim 13 wherein the affective disorder is selected from the group consisting of general anxiety disorder, panic disorder, obsessive compulsive disorder, depression and social phobia.

16. The method of treatment according to claim 12 wherein the living animal is a human.

17. The method of treatment according to claim 13 wherein the living animal is a human.

* * * * *